US00PP18990P3

(12) United States Plant Patent
Meilland

(10) Patent No.: US PP18,990 P3
(45) Date of Patent: Jun. 24, 2008

(54) FLORIBUNDA ROSE PLANT NAMED 'MEIGUIMOV'

(50) Latin Name: *Rosa hybrida*
Varietal Denomination: Meiguimov

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 11/518,913

(22) Filed: Sep. 12, 2006

(65) Prior Publication Data

US 2007/0180588 P1 Aug. 2, 2007

(30) Foreign Application Priority Data

Jan. 30, 2006 (EP) ..... 2006/0323

(51) Int. Cl.
*A01H 5/00* (2006.01)

(52) U.S. Cl. ..... Plt./148

(58) Field of Classification Search ..... Plt./148, Plt./141, 143, 107

See application file for complete search history.

*Primary Examiner*—Kent L Bell
*Assistant Examiner*—June Hwu
(74) *Attorney, Agent, or Firm*—Buchanan Ingersoll & Rooney PC

(57) ABSTRACT

A new and distinct variety of Floribunda rose plant is provided which abundantly forms on a nearly continuous basis attractive white blossoms with pink suffusion having five petals and decorative stamens. The plant exhibits very strong vegetation, a bushy growth habit, dense dark green foliage with a glossy aspect, and good tolerance to Marsonia. The attractive dark green glossy foliage contrasts nicely with the light blossom coloration. The new variety is particularly well suited for growing as attractive ornamentation in parks and gardens.

1 Drawing Sheet

Figures 1, 2, 3, 4, 5, 6, 7, 8, 9, 10, 11, 12, 13, 14, 15, 16:
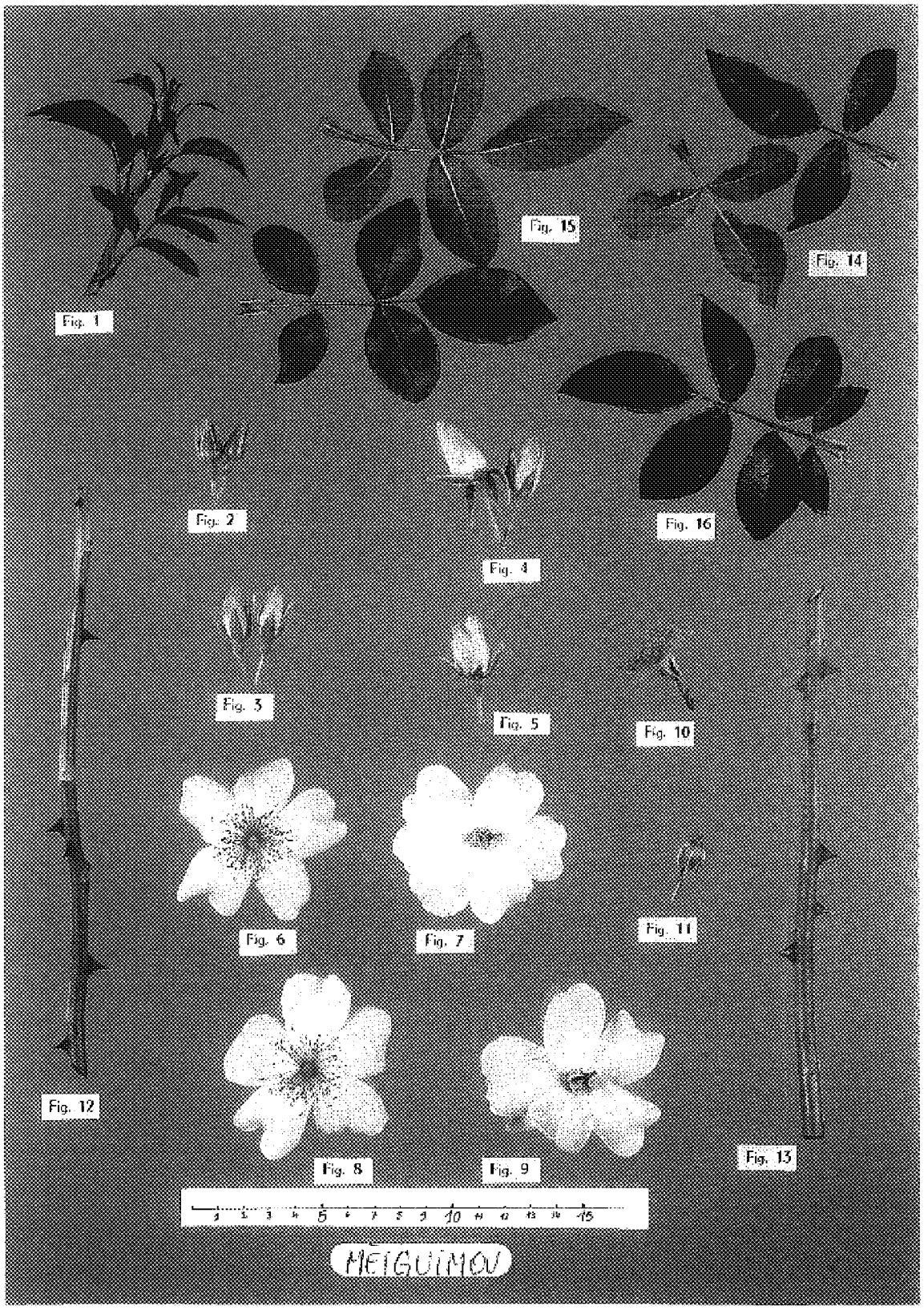

Botanical/commercial classification: *Rosa hybrida*/Floribunda Rose Plant.
Varietal denomination: cv. Meiguimov.

SUMMARY OF THE INVENTION

The new variety of *Rosa hybrida* Floribunda rose plant was created by artificial pollination wherein two parents were crossed which previously had been studied in the hope that they would contribute the desired characteristics. The female parent (i.e., the seed parent) was the product of the cross of the 'Meidomonac' variety (U.S. Plant Pat. No. 5,105) and the 'Playboy' variety (non-patented in the United States). The male parent (i.e., the pollen parent) was the 'Meinoiral' variety (non-patented in the United States). The parentage of the new variety can be summarized as follows:

('Meidomonac'×'Playboy')×'Meinoiral'.

The seeds resulting from the above pollination were sown and small plants were obtained which were physically and biologically different from each other. Selective study resulted in the identification of a single plant of the new variety.

It was found that the new Floribunda rose plant of the present invention:

(a) exhibits a bushy growth habit, (b) abundantly forms on a nearly continuous basis attractive white blossoms with pink suffusion having five petals and decorative stamens, (c) forms dense dark green foliage having a glossy aspect that contrasts well with the light blossom coloration, and (d) is particularly well suited for growing as attractive ornamentation in parks and gardens.

The disease tolerance is good particularly with respect to Marsonia.

The new variety well meets the needs of the horticultural industry and can be grown to advantage in the landscape where attractive ornamentation is desired.

The new variety can be readily distinguished from its ancestors. For instance, the 'Meidomonac' variety displays double medium pink blossoms. The 'Playboy' variety displays scarlet flowers with a pink eye, and the 'Meinoiral' variety forms considerably larger flowers.

Also, the new variety of the present invention can be readily distinguished from other previously known Floribunda rose varieties, such as the 'Betty Prior' variety (U.S. Plant Pat. No. 340) and the 'Sally Holmes' variety (non-patented in the United States). Unlike the new variety, the 'Betty Prior' variety forms carmine pink blossoms, and the 'Sally Holmes' variety forms creamy white blossoms.

The new variety has been found to undergo asexual propagation in France by a number of routes, including budding, grafting, and the use of cuttings. Asexual propagation by the above-mentioned techniques in France has shown that the characteristics of the new variety are stable and are strictly transmissible by such asexual propagation from one generation to another.

The new variety has been named 'Meiguimov'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately two years of age and were observed during June while budded on *Rosa froebelli* understock and growing outdoors at Le Cannet des Maures, Var, France. Dimensions in centimeters are indicated at the bottom of the photograph.

FIG. 1 — illustrates a specimen of a young shoot;

FIG. 2 — illustrates specimens of two floral buds before the opening of the sepals;

FIG. 3 — illustrates specimens of two floral buds at the opening of the sepals;

FIG. 4 — illustrates specimens of two floral buds at the opening of the petals;

FIG. 5 — illustrates a specimen of a flower in the course of opening;

FIG. 6 — illustrates a specimen of an open flower — plan view — obverse;

FIG. 7 — illustrates a specimen of an open flower — plan view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch;

FIG. 14 — illustrates specimens of leaves with three leaflets — plan view — upper surface (upper right) and — under surface (lower left);

FIG. 15 — illustrates specimens of leaves with five leaflets — plan view — upper surface (top right) and — under surface (bottom left); and FIG. 16 — illustrates a specimen of a leaf with seven leaflets — plan view — upper surface.

DETAILED DESCRIPTION

The chart used in the identification of the colors is that of The Royal Horticultural Society (R.H.S. Colour Chart). The description is based on the observation of two-year-old plants during June while budded on *Rosa froebelli* understock and growing outdoors at Le Cannet des Maures, Var, France.

Class: Floribunda.

Plant:

*Height.*—Approximately 60 to 90 cm on average at the end of the growing season.

*Width.*—Approximately 60 to 90 cm on average at the end of the growing season.

*Habit.*—Bushy.

Branches:

*Color.*—Young stems: near Yellow-Green Group 146C and 146D. Adult wood: near Yellow-Green Group 146C.

*Texture.*—Young stems and adult wood commonly are smooth with prickles as described hereafter.

*Thorns.*—On young stems. Small prickles; commonly absent. Long prickles: Configuration: very elongated and curved downwards on the upper surface, concave on the under surface, and oboval at the base. Quantity: approximately 7 on average on a stem length of 15 cm. Length: approximately 6 mm or more on average. Color: near Yellow-Green Group 144A and 144B and amply suffused with Greyed-Red Group 178A. On adult stems: Small prickles: commonly absent. Long prickles: Configuration: very elongated and curved downwards on the upper surface, concave on the under surface, and oboval at the base. Quantity: approximately 3 on average on a stem length of 15 cm. Length: approximately 6 mm or more on average. Color: near Yellow-Green Group 144B and amply suffused with near Greyed-Orange Group 165B and Greyed-Red Group 178A.

Leaves:

*Size.*—A five-leaflet leaf commonly is approximately 10.9 cm in length on average and approximately 9.4 cm in width on average.

*Stipules.*—Adnate, pectinate, and broad, and commonly display a length of approximately 2.3 cm and a width of approximately 0.4 cm. The upper surface commonly is near Green Group 137A, and the under surface commonly is near Yellow-Green Group 146C.

*Petioles.*—Upper surface: are glandular in texture, and near Green Group 137A in coloration. Under surface: commonly bear a very few prickles, and are near Yellow-Green Group 146C in coloration. Length: approximately 3.6 cm for the terminal leaflet.

*Rachis.*—Upper surface: is glandular in texture, and is near Green Group 137A in coloration. Under surface: commonly bears a very few prickles, and is near Yellow-Green Group 146C in coloration.

*Leaflets.*—Number: 3, and most often 5 and 7. Shape: generally elliptic with an obtuse base and a pointed tip. Size: the terminal leaflets commonly are approximately 5.3 cm in length and approximately 2.6 cm in width on average. Margin: with very weak undulation. Serration: small and single (as illustrated). Texture; physically firm and thick. Apex: acute to slightly cuspidate. Base: obtuse to rounded. General appearance: glossy, dense, dark green, and relatively thick. Color (young foliage): Upper surface: near Yellow-Green Group 146B amply suffused with Greyed-Red Group 178A and sometimes margined with near Greyed-Red Group 178A. Under surface: near Yellow-Green Group 146B and amply suffused with near Greyed-Red Group 178A. Color (adult foliage): Upper surface: near Green Group 137A. Under surface: near Yellow-Green Group 146A.

Inflorescence:

*Number of flowers.*—Pluriflorous, and commonly 3 to 20 blossoms per flowering stem.

*Peduncle.*—Glandular, pubescent, near Yellow-Green Group 146B, approximately 1.6 cm in length, of suffucient strength to well sustain the flower and approximately 0.2 cm in diameter.

*Sepals.*—Upper surface: smooth and near Yellow-Green Group 146D in coloration. Under surface: tomentose and near Yellow-Green Group 144B in coloration. Configuration: approximately 1.8 cm in length on average, and approximately 0.6 cm in width on average at the widest point.

*Buds.*—Shape: conical. Size: small. Length: approximately 1.6 cm on average. Width: approximately 0.9 cm on average at the widest point. Color: Upper surface: near Red Group 54C suffused with near Red Group 54B as the calyx breaks. Under surface: near Red Group 54C and amply suffused with near Red Group 54D as the calyx breaks. Basal spot: near Yellow-Green Group 154D on both surfaces as the calyx breaks.

*Flower.*—Shape: flat, cup-shaped. Diameter: approximately 5.4 cm on average. Color (in the course of opening): Upper surface: near Red Group 56D and more or less suffused with near Red Group 56B and 56C, and sometimes margined with near Red Group 54B. Under surface: near Red Group 56D and more or less suffused with near Red Group 56B and 56C, and sometimes margined with near Red Group 54B. Basal petal spot: very small and near White Group 155B on both surfaces. Color (when fully open): Upper surface: near Red Group 56D and more or less suffused with near Red Group 56B and 56C, and sometimes margined with near Red Group 54B. Under surface: near Red Group 56D and more or less suffused with near Red Group 56B and 56C, and sometimes margined with near Red Group 54B. Basal petal spot: very small and near White Group 155B on both surfaces. Color stability: very slight discoloration with age. Fragrance: none. Lasting quality: the blossoms commonly last approximately 12 to 14 days on average on the plant, and approximately 7 to 10 days on average when cut and placed in a vase. Petal number: five under normal growing conditions. Petal shape: cordate. Petal texture: consistent and somewhat firm. Petal arrangement: imbricated; and without petaloids. Petal drop: good with the petals commonly detaching cleanly. Stamen number: approximately 121 on average. Anthers: regularly arranged around the styles, approximately 0.2 cm in size on average, and near Greyed-Orange Group 165B to near Greyed-Orange Group 167B depending upon the level of maturity. Pollen: present and near Greyed-Orange Group 167C in coloration. Filaments: approximately 1 cm in length on average and near Red-Purple Group 58A in coloration. Pistils: approximately 17 on average. Stigmas: approximately 0.1 cm in size on average and near Greyed-Orange Group 164A in coloration. Styles: approximately 0.2 cm in length on average, and near Red-Purple Group 60B in coloration. Receptacle: smooth, pitcher-shaped in longitudinal section, approximately 0.6 cm in length on average, approximately 0.4 cm in width on average at the widest point, and near Yellow-Green Group 146B in coloration. Hips: smooth, generally pear-shaped, approximately 1.2 cm in length on average. approximately 1 cm in width on average, and near Yellow-Green Group 146B in coloration.

Development:

*Vegetation.*—Very strong.

*Blooming.*—Early, abundant and nearly continuous.

*Resistance to diseases.*—Good, particularly with respect to Marsonia.

*Aptitude to bear fruit.*—Sparse to medium.

I claim:

1. A new and distinct Floribunda rose plant characterized by the following combination of characteristics:

(a) exhibits a bushy growth habit, (b) abundantly forms on a nearly continuous basis attractive white blossoms with pink suffusion having five petals and decorative stamens, (c) forms dense dark green foliage having a glossy aspect that contrasts well with the light blossom coloration, and (d) is particularly well suited for growing as attractive ornamentation in parks and gardens;

substantially as herein shown and described.

* * * * *

MEIGUIMOU